United States Patent [19]
Klein

[11] Patent Number: 4,892,092
[45] Date of Patent: Jan. 9, 1990

[54] FACIAL MASK FOR USE IN EFFECTING ISOMETRIC TONING OF FACIAL MUSCLES

[76] Inventor: Sidi Klein, Hadganiot Street 6, Rehovot, Israel

[21] Appl. No.: 78,633

[22] Filed: Jul. 28, 1987

Related U.S. Application Data

[63] Continuation-in-part of Ser. No. 826,796, Feb. 6, 1986, abandoned, which is a continuation-in-part of Ser. No. 566,033, Dec. 27, 1983, abandoned.

[51] Int. Cl.⁴ ............................................. A61F 5/08
[52] U.S. Cl. ................................. 128/76 B; 128/76 R
[58] Field of Search .................. 2/9; 128/76 B, 76 R, 128/206.29, 380, 733; D29/13, 16, 17

[56] References Cited

U.S. PATENT DOCUMENTS

| D. 198,359 | 6/1964 | McLeod | D29/16 |
|---|---|---|---|
| D. 202,097 | 8/1965 | Gilbert | D29/13 |
| D. 215,685 | 10/1969 | Helmer | D29/17 |
| 460,301 | 9/1891 | Cumnock | 2/9 |
| 1,665,386 | 4/1928 | Walmer | 2/9 |
| 2,520,773 | 8/1950 | Muller | 128/76 R |
| 3,346,875 | 10/1967 | Weisberger | 2/9 |
| 3,373,443 | 3/1968 | Marietta | 2/9 |
| 4,098,270 | 7/1978 | Dolby | 128/206.29 |
| 4,155,352 | 5/1979 | Toglia | 128/733 |
| 4,189,141 | 2/1980 | Rooney | 128/76 B |
| 4,325,386 | 4/1982 | Katz | 128/733 |
| 4,359,724 | 11/1982 | Zimmerman | 128/733 |
| 4,619,266 | 10/1986 | Hodgson | 128/733 |
| 4,689,836 | 9/1987 | Vitaloni | 2/9 |

FOREIGN PATENT DOCUMENTS

| 619535 | 5/1961 | Canada | 2/9 |
|---|---|---|---|
| 2948059 | 7/1981 | Fed. Rep. of Germany | 128/380 |
| 3441151 | 7/1985 | Fed. Rep. of Germany | 128/733 |
| 201401 | 8/1923 | United Kingdom | 2/9 |

*Primary Examiner*—David A. Wiecking
*Assistant Examiner*—Aaron J. Lewis
*Attorney, Agent, or Firm*—Benjamin J. Barish

[57] ABSTRACT

A facial mask for use in effecting isometric toning of facial muscles comprises a plurality of shaped pressure applicators located to overlie the termination points of selected facial muscles, and an expansible chamber located such that when the chamber is expanded, it causes the pressure applicators to apply pressure to the termination points of the selected facial muscles. The facial mask may further include a mouthpiece to be received in the user's mouth and to be bitingly engaged by the user's teeth for anchoring the user's mastication muscles and for tensioning the user's facial muscles around the lips during use of the device. The pressure applicators may also include surface electrodes for sensing EMG (electromyogram) signals produced by the muscles to provide an indication of whether the proper muscles are being exercised.

18 Claims, 3 Drawing Sheets

FACIAL MASK FOR USE IN EFFECTING ISOMETRIC TONING OF FACIAL MUSCLES

RELATED APPLICATION

The present application is a continuation-in-part of pending Application Ser. No. 826,796, filed 2/6/86 and now abandoned 8/7/87, which in turn is a continuation-in-part of Application Ser. No. 06/566,033 filed Dec. 27 1983, now abandoned.

BACKGROUND OF THE INVENTION

The present invention relates to a facial mask for use in effecting isometric toning of facial muscles.

One of society's long standing cosmetic problems relates to facial-sagging and wrinkling of the skin, especially in the face and neck. Many different approaches have been employed to eliminate such problems. Some people have expensive facelifts; others utilize expensive cosmetics and lotions; and still others utilize various dietetic and assorted paraphernalia.

Lack of tone in the facial tissue and muscles contributes to facial sagging and skin wrinkling. One well-known muscle-toning technique is isometric exercise. In this exercise, the muscle acts against resistance, and the muscle strain tends to cause the muscles to become toned after repeated exercises.

The prior art includes numerous patents illustrating various facial masks for reducing face wrinkles. Bergman Italian Patent No. 573706 discloses an eyeglass type device for this purpose. Robins U.S. Pat. No. 3,507,493 discloses an eye and forehead area muscle exerciser, in which a portion of the face is covered by the device to hold the facial muscles against movement. Rooney U.S. Pat. No. 4,189,141 also discloses a mask which completely covers the face, and which has pockets in which weights may be placed while the facial muscles are exercised. Other prior art devices are large in size covering most of the muscle area sought to be exercised. As a consequence, the skin of the wearer is tightly covered providing discomfort to the wearer because of the weight and because the wearer's skin cannot breathe. Thus, none of these devices has come into widespread use.

BRIEF SUMMARY OF THE INVENTION

An object of the present invention is to provide a new facial mask for use in effecting isometric toning of facial muscles.

According to one feature of the present invention, the facial mask comprises: a plurality of shaped pressure applicators located to overlie the termination points of selected facial muscles of the user when applied to the user's head; at least one expansible chamber located such that when the chamber is expanded, it causes the pressure applicators to apply pressure to the termination points of the selected facial muscles; and a hand-operated fluid pump for manually pumping fluid into the expansible chamber to expand it and thereby to cause the pressure applicators to apply pressure to the termination points of the selected facial muscles.

The expansible chamber may be carried by the facial mask to overlie the back of the user's head; alternatively, or in addition, at least some of the shaped pressure applicators are formed as expansible chambers. In the preferred embodiment disclosed below, an expansible chamber is carried by the facial mask to overlie the back of the user's head, and all the shaped pressure applicators are formed as expansible chambers.

According to another feature in the described preferred embodiment, the facial mask includes an upper band section having a plurality of the pressure applicators configured to enclose the upper part of the user's head to overlie the user's eyes; and a depending lower section including a pair of arms joined at their outer ends to the upper band section at points outwardly of the eye portions and joined together at their inner ends forming an intermediate portion also having a plurality of pressure applicators to overlie the user's mouth.

In the described preferred embodiment, the pair of arms of the lower depending section are pivotably mounted to the upper band section to permit pivoting the two sections to a folded condition for storage or transportation.

According to a still further feature in the described preferred embodiment, the shaped pressure applicators include a narrow strip located to extend just above the user's eyelashes from one side of the face to the other side to overlie the termination points of the frontalis; strips of inclined V-shape located to extend at each side of the user's face starting from a point laterally of each eye and diverging outwardly, to overlie the lateral angle of the orbicularis occuli; strips located to extend laterally below each of the user's eyes to overlie the juncture of the zigomatic major blend with the orbecularis occuli; and strips of inclined V-shape located to extend at each side of the user's mouth and diverging inwardly to cover the termination points of the muscles of the opposite side of the user's mouth.

According to another feature of the invention, the facial includes a mouthpiece to be received in the user's mouth and to be bitingly engaged by the user's teeth for anchoring the user's mastication muscles during use of the device. According to a further feature, the mouthpiece includes a hollow tubular lip-engaging member to be tightly enclosed by the user's lips during use of the device.

According to a still further feature, at least some of the pressure applicators include surface electrodes for sensing EMG (electromyogram) signals produced by the muscles to provide an indication of whether the proper muscles are being exercised.

The facial mask made in accordance with the present invention takes advantage of the fact that muscles are attached to the anatomical frame at points of insertion and origin (termination points). Unlike most skeletal muscles, the facial muscles often insert into the skin at their termination points. When the termination points are fixed, the facial muscles can be effectively toned by simply attempting to contract the muscles in a normal manner. Thus, as the muscles are held fixed at their termination points to restrain their shortening, the muscles are toned isometrically. Furthermore, by holding the specific insertion points fixed, a maximal isometric effect is realized because the isometric work at each point along the muscle is a multiple of the distance and the contracting forces from the fixed point.

Thus, rather than randomly applying pressure to the face, as done by large unwieldy masks, the present invention applies pressure to specific areas of the facial muscles while minimizing the amount of facial surface covered during the exercises. Toning of the facial muscles can thus be achieved to prevent or reduce wrinkling.

BRIEF DESCRIPTION OF THE DRAWINGS

The invention is herein described, by way of example only, with reference to the accompanying drawnings, in which.

DESCRIPTION OF PREFERRED EMBODIMENTS

Figure 3:
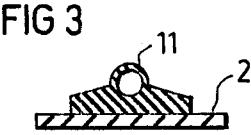
FIG. 3 is a sectional view along lines III—III of FIG. 1.
Figure 4:
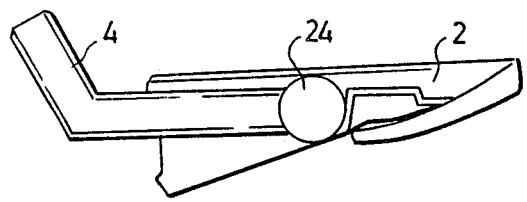
FIG. 4 illustrates the mask of FIGS. 1-3 in folded compact form for transportation or storage.

The facial mask illustrated in FIGS. 1-5 of the drawings is constituted of two sections, namely an upper band section 2 configured to enclose the upper part of the user's head and to overlie the user's eyes; and a depending lower section 4. Lower section 4 includes a pair of arms 4a, 4b joined at their outer ends to the upper band section at points outwardly of the eye portions, and joined together at their inner ends forming an intermediate portion 4c to overlie the user's mouth. Both sections 2 and 4 of the facial mask are preferably made of rigid material, such as rigid plastic. The two arms, 4a, 4b of the lower section 4 are pivotably mounted at 6, 7 to the upper band section 2 to permit pivoting the two sections to a folded condition, as illustrated in FIG. 4, for storage or transportation when the facial mask is not in use.

Each of the two sections 2, 4 of the illustrated facial mask includes a plurality of shaped pressure applicators located to overlie the termination points of selected facial muscles of the user when applied to the user's head. In addition, the facial mask includes at least one expansible chamber located such that when the chamber is expanded, it causes the pressure applicators to apply pressure to the termination points of the selected facial muscles. In the preferred embodiment of the invention illustrated in the drawings, the facial mask includes an expansible chamber at the rear side of the upper band section 2 to overlie the back of the user's head; in addition, the pressure applicators themselves are all constructed as expansible chambers adapted to be inflated to apply pressure to the termination points of the selected muscles.

Figure 2:
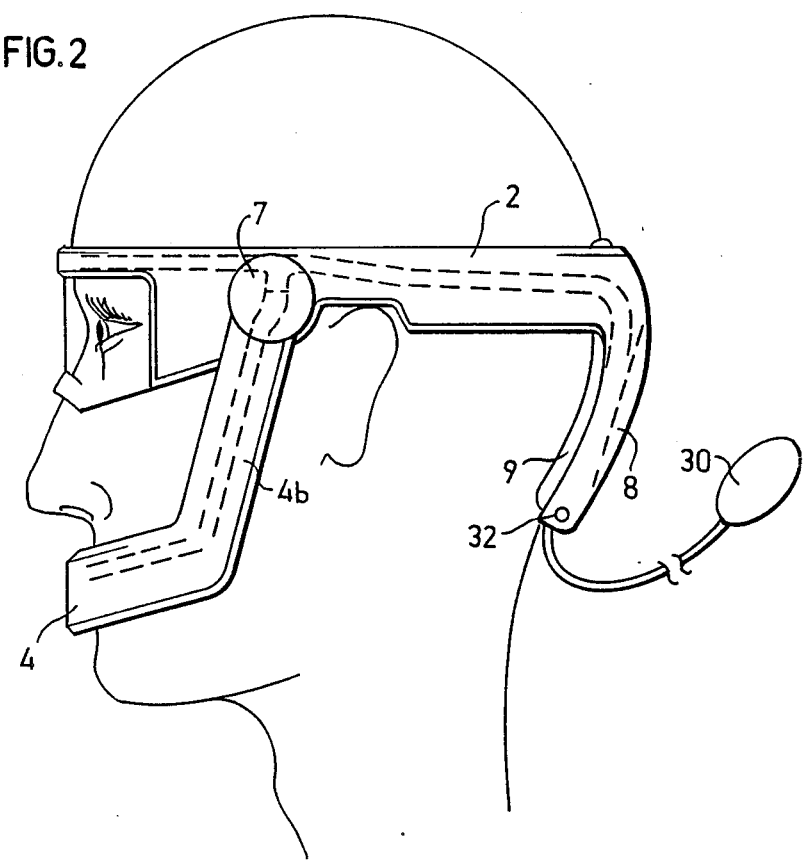
FIG. 2 is a side elevational view illustrating the facial mask of FIG. 1.

More particularly, the rear side of the upper band section 2 is formed with a depending portion 8, as shown in FIG. 2, to overlie the base of the user's head at the juncture with the user's neck. Portion 8 of the band section 2 is provided with an inflatable bag 9 defining an expansible chamber which, when inflated, presses against the back of the user's head to force the front of the band section 2 firmly against the user's face.

The pressure applicators located in the front part of the head band section 2, and in the lower depending section 4, are of hollow-construction, as shown in FIG. 3, to enable them also to serve as expansible chambers and to apply localized pressure to selected areas of the user's face when they are expanded by the introduction of pressurized fluid into them. These localized areas are the termination points of selected facial muscles contacted by the pressure applicators as follows:

The upper band section 2 includes a first pressure applicator 11 in the form of a narrow strip located to extend just above the user's eyelashes from one side of the face to the other, to overlie the termination points of the frontalis. Two further pressure applicators 12 are provided at each side of the user's face, and are in the form of strips of inclined V-shape located to extend at the respective side of the user's face starting from a point laterally of each eye and diverging outwardly to overlie the lateral angle of the orbicularis occuli. A further pressure applicator 13 is provided at each side of the user's face and is in the form of a strip located to extend laterally below each of the user's eyes and to overlie the junctures of the zigomatic major blend with the orbecularis occuli. A further pressure applicator 14 is located centrally along the lower edge of the upper band section 2 to extend across the ridge of the user's nose over the transverse part of the nasalis.

The lower depending section 4 of the facial mask includes pressure applicators 15-18 located to overlie the termination points of the mouth muscles. These applicators include: a strip 15 at each side of the user's mouth starting from just laterally below the end of the user's nose and inclined downwardly and outwardly so as to overlie the juncture between the orbiculus oris and the lavator labii sup; a further strip 16 located at each side of the user's mouth and forming, with its respective pressure applicator 15, an inclined-V diverging inwardly towards the user's mouth to overlie the juncture of the depressor angule oris, depressor labii inf., and the mentalis with the orbiculus oris; a pad 17 overlying the juncture of applicators 15 and 16 and located to overlie the buccinator; and a further pad 18 of circular configuration located to overlie the user's lips.

All the pressure applicators 11-18 are made of elastomeric material, such as natural or synthethic rubber, and are of hollow construction, as shown particularly in FIG. 3, such that when pressurized fluid is applied, the pressure applicators expand to apply the localized pressure to the selective areas of the user's face covered by the applicators. This applied fluid may be air or a liquid, e.g., water.

Figure 1:
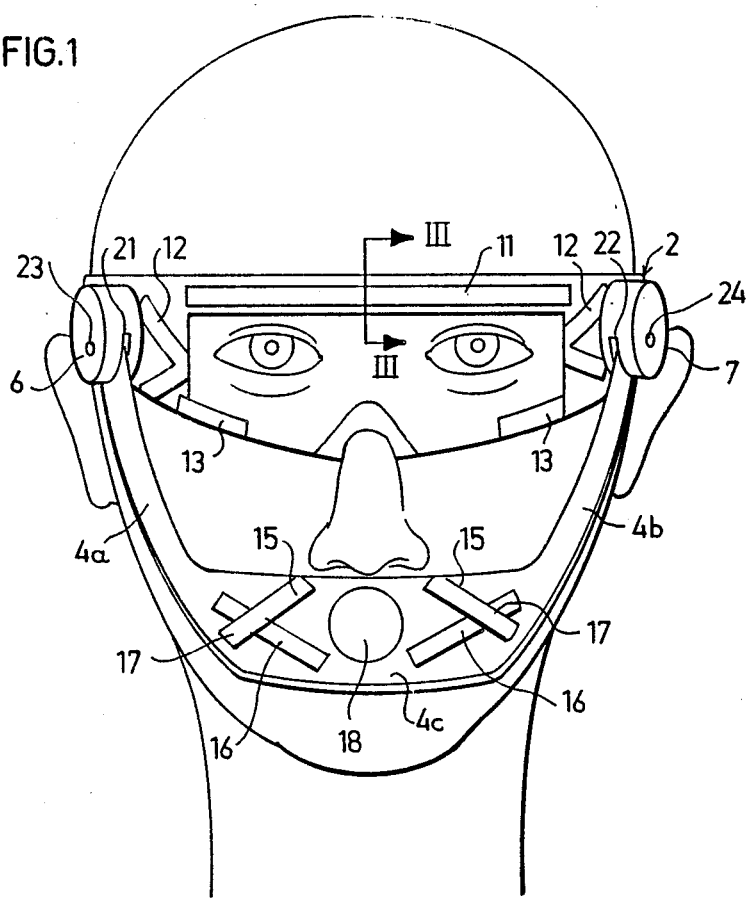
FIG. 1 is a front view illustrating one form of facial mask cotstructed in accordance with the present invention.

The pivotable connections 6, 7, mounting the lower depending section 4 of the facial mask to the upper band section 2, are solid discs integral with the upper band section 2 but are formed with slots 21, 22 of a width corresponding to the width of the ends of the arms 4a, 4b. The arms are pivotably mounted on pins 23, 24 passing through the discs 6, 7 and the ends of the arms 4a, 4b. The slots 21, 22 are configured such that the arms 4a, 4b limit against their ends when the lower mask section 4 is in its fully opened position as illustrated in FIGS. 1 and 2, but permit the arms to be pivotted to a closed folded position, as shown in FIG. 4, to form a compact unit convenient for storage or carrying when the mask is not in use.

The inflatable chamber 9 at the rear end of the mask, and the pressure applicators 11–18, are inflated manually by a hand-pump 30 (FIGS. 2, 5) connected to a port 32 (FIG. 2) in the rear portion 8 of the upper band section 2.

Figure 5:
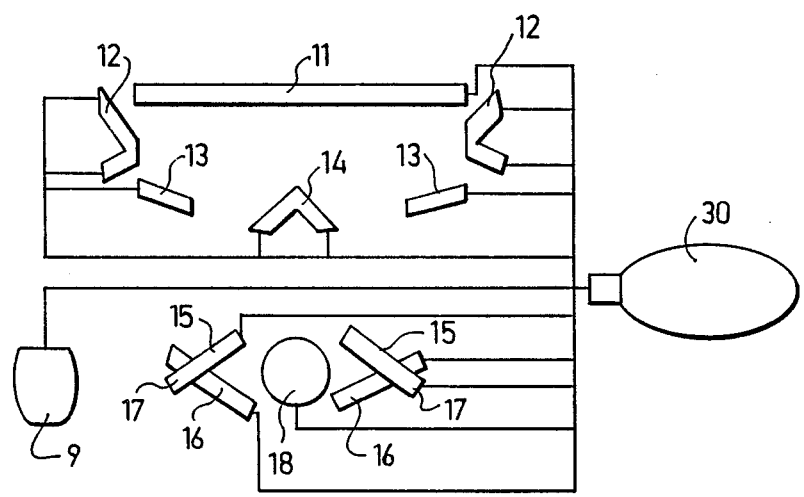
FIG. 5 is a diagram illustrating the fluid circuit in the facial mask of FIG. 1-4.

FIG. 5 illustrates the fluid connections from the hand-pump 30 to the inflatable chambers 9 and 11–18 such that when the hand-pump is manually operated, all the foregoing chambers are inflated. The inflation of chamber 9 presses the front part of the band section 2, and also the lower depending section 4, firmly against the face of the user, while the inflation of the pressure applicators 11–18 applies localized pressure to the termination points of the facial muscles as described above. These localized pressures thus immobilize the ends of the muscles, permitting the muscles to be toned through isometric exercises. Since only the muscle ends are thus immobilized, the muscles themselves are permitted to contract by exercises, while their ends are held fixed by the pressure applicators. This enhances the isometric toning, and also reduces discomfort, as compared to the prior art masks which generally cover the complete muscles themselves, rather than the muscle ends.

Figure 6:
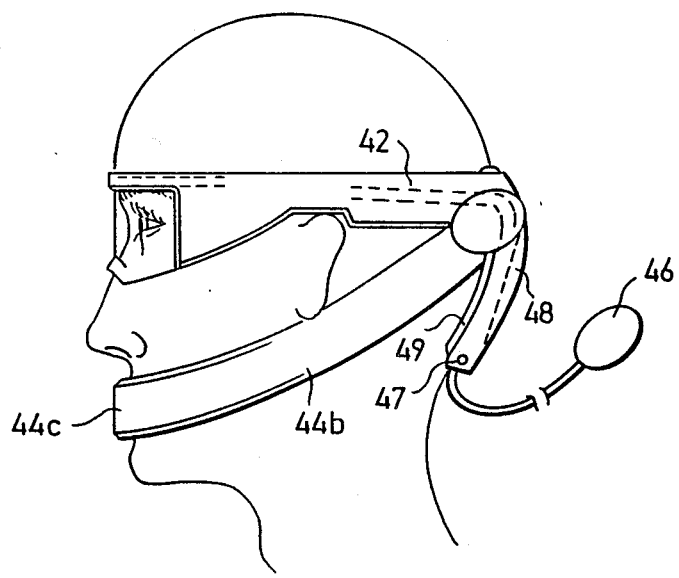
FIG. 6 is a side elevational view illustrating a modification in the construction of the facial mask.

FIG. 6 illustrates a variation in the construction of the facial mask. The mask in FIG. 6 also includes an upper band section 42 configured to enclose the upper part of the user's head and to overlie the user's eyes, and a depending lower section 44 formed with a pair of arms 44b joined at their upper ends to the upper band section and at their inner ends to an intermediate portion 44c overlying the user's mouth. In the modification of FIG. 6, the pair of arms 44b are pivotably mounted to the upper band section 42 at the back of the band portion, rearwardly of the user's ears, rather than at points between the user's eyes and ears as in FIGS. 1 and 2. The facial mask of FIG. 6 is otherwise constructed, and operates in the same manner, as that of FIGS. 1 and 2, and includes a manually-operable hand-pump 46 connected to a port 47 in the rear portion 48 of the upper band section 42 to inflate bag 49 defining an expansible chamber which, when inflated, presses against the back of the user's head to force the front of the band section 42 firmly against the user's face.

Figure 7:
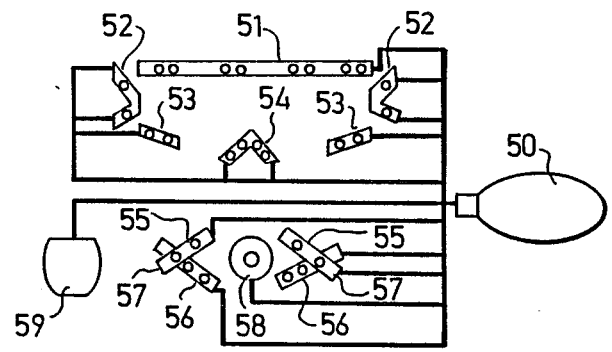
FIG. 7 is a diagram similar to that of FIG. 5 but illustrating surface electrodes applied to the pressure applicators.

FIG. 7 illustrates a further variation wherein the pressure applicators include surface electrodes for sensing EMG (electromyogram) signals produced by the muscles to provide an indication of whether the proper muscles are being exercised. The diagram illustrated in FIG. 7 is the same as in FIG. 5, except all the pressure applicators, indicated at 51–58 and corresponding to pressure applicators 11–18 in FIG. 5, are provided with electrodes 51'–58' for sensing the EMG signals. The diagram of FIG. 7 further includes a hand pump 50 for inflating chamber 59 at the rear end of the mask.

Figure 8:
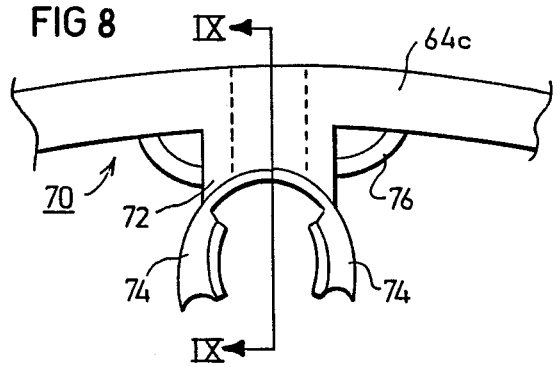
FIG. 8 is an enlarged fragmentary view illustrating a modification in the construction of the facial mask to incorporate a mouthpiece to be received in the user's mouth.
Figure 9:
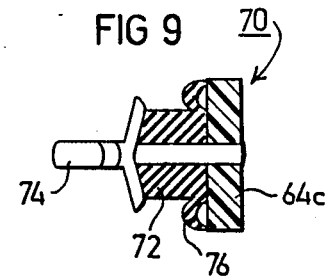
FIG. 9 is a sectional view along lines IX—IX of FIG. 8.

FIGS. 8 and 9 illustrate a further variation applicable to either of the facial mask constructions described earlier. Thus, in the variation of FIGS. 8 and 9, the intermediate portion of the lower section of the facial mask, corresponding to intermediate portion 4c of FIG. 1 and designated 64c in FIGS. 8 and 9, is provided with a mouthpiece, generally designated 70, to be received in the user's mouth and to be bitingly engaged by the user's teeth for anchoring the user's mastication muscles and also for tensioning the user's facial muscles around the lips, during use of the device.

Thus, mouthpiece 70 illustrated in FIGS. 8 and 9 comprises a hollow tubular member 72 secured to intermediate portion 64c of the lower section of the mask to be aligned with the user's mouth, and a teeth-engaging portion 74 of arcuate shape to be bitingly engaged by the user's teeth. The mouthpiece 70 further includes an annular flexible pad 76 circumscribing the tubular member 72 at its juncture with intermediate portion 64c, to be engaged by the user's lips.

In use, the user inserts the arcuate teeth portion 74 between his teeth with his lips enclosing tubular member 72 and pressed against annular pad 76, and firmly closes his jaws to bite the arcuate portion 74 of the mouthpiece between his teeth, while breathing through opening 78 through tubular member 72 and intermediate portion 64c of the lower part of the facial mask. This anchors the user's mastication muscles, and also tensions the user's facial muscles around the lips, during the use of the device, which has been found to improve the isometric toning of the facial muscles when the device is used in the manner otherwise described above with respect to FIGS. 1–5.

Many variations and modifications of the invention will be apparent. For example, the pressure applicators could be in the form of solid strips projecting from the interior of the mask such that the pressure is applied by these solid strips when the rear chamber 9 is inflated. In addition, the hand-pump for inflating the chambers could be carried by the mask itself in the form of a depressable knob, which is depressed and released in order to effect the pumping action.

Many other variations, modifications and applications of the invention will be apparent.

What is claimed is:

1. A facial mask for use in effecting isometric toning of facial muscles, comprising:
    a plurality of shaped pressure applicators located to overlie the termination points of selected facial muscles of the user when applied to the user's head;
    said facial mask including an upper band section having a plurality of said pressure applicators and configured to enclose the upper part of the uesr's head to overlie the user's eyes; and a depending lower section including a pair of arms joined at their outer ends to said upper band section at points outwardly of the eye portions and joined together at their inner ends forming an intermediate portion also having a plurality of pressure applicators to overlie the user's mouth;
    a rear expansible chamber carried by the facial mask to overlie the back of the user's head such that when the chamber is expanded, it causes said pressure applicators to apply pressure to the termination points of the selected facial muscles;
    and a hand-operated fluid pump for manually pumping fluid into said expansible chamber to expand it and thereby to cause said pressure applicators to apply pressure to the termination points of the selected facial muscles.

2. The facial mask according to claim 1, wherein at least some of said shaped pressure applicators are formed with expansible chambers connected to said rear expansible chamber so as to be expanded therewith.

3. The facial mask according to claim 1, wherein said pressure applicators of the upper band section are located to apply pressure to the termination points of the frontalis and the lateral angle of the orbicularis occuli; and wherein the pressure applicators of the lower section are located to apply pressure to the termination points of the user's mouth muscles.

4. The facial mask according to claim 3, wherein said pair of arms of the lower depending section are pivotably mounted to said upper band section to permit pivoting the two sections to a folded condition for storage or transportation.

5. The facial mask according to claim 1, wherein said shaped pressure applicators include one in the form of a narrow strip located to extend just above the user's eyelashes from one side of the face to the other side to overlie the termination points of the frontalis.

6. The facial mask according to claim 5, wherein said shaped pressure applicators include strips of inclined V-shape located to extend at each side of the user's face starting from a point laterally of each eye and diverging outwardly, to overlie the lateral angle of the orbicularis occuli.

7. The facial mask according to claim 6, wherein said shaped pressure applicators include a strip located to extend laterally below each of the user's eyes to overlie the juncture of the zigomatic major blend with the orbecularis occuli.

8. The facial mask according to claim 7, wherein said shaped pressure applicators include strips of inclined V-shape located to extend at each side of the user's mouth and diverging inwardly to cover the termination points of the muscles at the opposite sides of the user's mouth.

9. The facial mask according to claim 1, wherein said depending lower section includes a mouthpiece to be received in the user's mouth and to be bitingly engaged by the user's teeth for anchoring the user's mastication muscles during use of the device.

10. The facial mask according to claim 9, wherein said mouthpiece includes a hollow, tubular lip-engaging member to be tightly enclosed by the user's lips for tensioning the user's facial muscles around the lips during use of the device.

11. The facial mask according to claim 1, wherein at least some of said pressure applicators include surface electrodes for sensing EMG (electromyogram) signals produced by the muscles to provide an indication of whether the proper muscles are being exercised.

12. The facial mask according to claim 1, wherein said arms of the lower section are pivotably mounted to said upper band section at points to be located during use between the user's eyes and ears during the use of the facial mask.

13. The facial mask according to claim 1, wherein said arms of the lower section are pivotably mounted to said upper band section at points to be located during use readwardly of the user's ears.

14. A facial mask for use in effecting isometric toning of facial muscles comprising a plurality of shaped pressure applicators located to overlie the termination points of selected facial muscles of the user when applied to the user's head; said shaped pressure applicators including:
    a narrow strip located to extend just above the user's eyes from one side of the face to the other side to overlie the termination points of the frontalis;
    strips of inclined V-shape located to extend at each side of the user's face starting from a point laterally of each eye and diverging outwardly, to overlie the lateral angle of the orbicularis occuli;
    strips located to extend laterally below each of the user's eyes to overlie the juncture of the zigomatic major blend with the orbecularis occuli;
    and strips of inclined V-shape located to extend at each side of the user's mouth and diverging inwardly to cover the termination points of the muscles at the opposite side of the user's mouth.

15. The facial mask according to claim 14, further comprising:
    at least one expansible chamber located such that when the chamber is expanded, it causes said pressure applicators to apply pressure to the termination points of the selected facial muscles;
    and a hand-operated fluid pump for manually pumping fluid into said expansible chamber to expand it and thereby to cause said pressure applicators to apply pressure to the termination points of the selected facial muscles.

16. A facial mask for use in effecting isometric toning of facial muscles, comprising: a plurality of shaped pressure applicators located to overlie and press against the termination points of selected facial muscles of the user's face and around the user's lips when applied to the user's head; said facial mask including a mouthpiece to be received in the user's mouth and to be bitingly engaged by the user's teeth for anchoring the user's mastication muscles, and for tensioning the user's facial muscles around the lips, during the use of the device; an expansible chamber located such that when the chamber is expanded, it cause the pressure applicators to apply pressure to the termination points of the selected facial muscles; and a hand-operated fluid pump for manually pumping fluid into said expansible chamber to expand it and thereby to cause said pressure applicators to apply pressure to the termination points of the selected facial muscles.

17. The facial mask according to claim 16, wherein said mouthpiece includes a hollow tubular lip-engaging member to be tightly enclosed by the user's lips, and an annular flexible pad circumscribing the tubular member to be engaged by the user's lips, during the use of the device.

18. The facial mask according to claim 16, further including surface electrodes carried by said pressure applicators for sensing EMG (electromyogram) signals produced by the muscles to provide an indication of whether the proper muscles are being exercised.

* * * * *